United States Patent
Brown et al.

(10) Patent No.: US 7,100,801 B2
(45) Date of Patent: *Sep. 5, 2006

(54) DUAL DISPENSER, SUPPLY UNIT, AND METHOD

(75) Inventors: Douglas S. Brown, Toledo, OH (US); David F. Scherger, Toledo, OH (US); George C. Heilman, Northwood, OH (US); Robert B. Brown, Toledo, OH (US)

(73) Assignee: Fresh Products, Inc., Toledo, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/795,973

(22) Filed: Mar. 8, 2004

(65) Prior Publication Data
US 2004/0251273 A1    Dec. 16, 2004

Related U.S. Application Data

(63) Continuation of application No. 10/253,348, filed on Sep. 24, 2002, now Pat. No. 6,729,506, which is a continuation of application No. 09/544,011, filed on Apr. 6, 2000, now abandoned, which is a continuation of application No. 09/019,252, filed on Feb. 5, 1998, now Pat. No. 6,062,425, which is a continuation of application No. 08/730,364, filed on Oct. 15, 1996, now Pat. No. 5,799,826, which is a continuation of application No. 08/319,292, filed on Oct. 6, 1994, now Pat. No. 5,595,324, which is a continuation of application No. 08/024,448, filed on Mar. 1, 1993, now Pat. No. 5,379,917.

(51) Int. Cl.
*B67D 5/00* (2006.01)

(52) U.S. Cl. .................. 222/105; 222/181.3; 222/325; 261/26; 261/30; 261/DIG. 65

(58) Field of Classification Search .................. 222/4, 222/105, 129, 135, 180, 181.3, 325, 642; 261/26, 30, DIG. 65
See application file for complete search history.

(56) References Cited

U.S. PATENT DOCUMENTS 2,925,202 A    2/1960    Stevens (Continued)

FOREIGN PATENT DOCUMENTS

| CH | 296864 | 5/1954 |
|----|--------|--------|
| DE | 461572 | 5/1928 |

*Primary Examiner*—Joseph A. Kaufman
(74) *Attorney, Agent, or Firm*—Knobbe, Martens, Olson & Bear, LLP

(57) ABSTRACT

A method of facilitating replacement of a supply of air freshener every time a supply of soap is replaced, including the steps of providing a supply of air freshener, providing a supply of soap and joining the supply of soap and the supply of air freshener. Another aspect of the invention is a method of packaging a supply unit including providing a supply of soap and a supply of air freshener and connecting the supply of soap and the supply of air freshener in a manner such that when the supply of soap is removed from a dispenser, the supply of air freshener is removed from the dispenser as well. Another aspect is a supply unit for the dual dispenser including a receptacle, a supply of soap within the receptacle, and a supply of air freshener connected to or secured within the receptacle. Yet another aspect of the invention is a dual dispenser including means for dispensing the soap, means for actuating the dispensement of soap, means for accelerating the dispensement of air freshener and means for actuating the means for accelerating the dispensement of air freshener.

5 Claims, 7 Drawing Sheets

U.S. PATENT DOCUMENTS

| | | |
|---|---|---|
| 3,363,807 A * | 1/1968 | Powell ........................ 222/105 |
| 3,380,632 A | 4/1968 | Wilson |
| 3,522,935 A | 8/1970 | Lewis |
| 3,729,553 A | 4/1973 | Gold et al. |
| 3,993,444 A | 11/1976 | Brown |
| 4,154,375 A | 5/1979 | Bippus |
| 4,294,778 A | 10/1981 | DeLuca |
| 4,516,692 A * | 5/1985 | Croley ........................ 222/105 |
| 4,548,351 A * | 10/1985 | Gusic ........................ 229/122.1 |
| 4,549,693 A | 10/1985 | Barlics |
| 4,570,827 A | 2/1986 | Roggenburg, Jr. et al. |
| 4,664,312 A | 5/1987 | Bryson |
| 4,741,461 A | 5/1988 | Williamson et al. |
| 4,743,406 A | 5/1988 | Steiner et al. |
| 4,830,791 A | 5/1989 | Muderlak et al. |
| 4,849,606 A | 7/1989 | Martens, III et al. |
| 4,881,652 A | 11/1989 | Schiemann |
| 4,903,584 A | 2/1990 | Styles |
| 4,921,131 A | 5/1990 | Binderbauer et al. |
| 4,946,070 A | 8/1990 | Albert et al. |
| 4,946,072 A | 8/1990 | Albert et al. |
| 4,955,508 A | 9/1990 | Capanna et al. |
| 4,967,935 A | 11/1990 | Celest |
| 5,023,020 A | 6/1991 | Machida et al. |
| 5,050,775 A * | 9/1991 | Marquardt ........................ 222/93 |
| RE33,864 E | 3/1992 | Steiner et al. |
| 5,102,015 A | 4/1992 | Barnard et al. |
| 5,147,582 A | 9/1992 | Holzner, Sr. et al. |
| 5,186,359 A * | 2/1993 | Brown et al. ........................ 222/1 |
| 5,195,661 A * | 3/1993 | Light ........................ 222/105 |
| 5,265,772 A | 11/1993 | Bartasevich et al. |
| 5,324,490 A | 6/1994 | Van Vlahakis et al. |
| 5,328,646 A | 7/1994 | Bryson et al. |
| 5,379,917 A | 1/1995 | Brown et al. |
| 5,392,379 A | 2/1995 | Fussell |
| 5,406,320 A * | 4/1995 | Durst et al. ........................ 347/86 |
| 5,595,324 A | 1/1997 | Brown et al. |
| 5,799,826 A | 9/1998 | Brown et al. |
| 6,062,425 A | 5/2000 | Brown et al. |
| 6,729,506 B1 * | 5/2004 | Brown et al. ........................ 222/325 |

\* cited by examiner

DUAL DISPENSER, SUPPLY UNIT, AND METHOD

RELATED APPLICATIONS

The present application is a continuation of U.S. patent application Ser. No. 10/253,348, filed Sep. 24, 2002, now U.S. Pat. No. 6,729,506, which is a continuation of U.S. patent application Ser. No. 09/544,011, filed Apr. 6, 2000, abandoned, which is a continuation of U.S. patent application Ser. No. 09/019,252, filed Feb. 5, 1998, now U.S. Pat. No. 6,062,425, which is a continuation of U.S. patent application Ser. No. 08/730,364, filed Oct. 15, 1996, now U.S. Pat. No. 5,799,826, which is a continuation of U.S. patent application Ser. No. 08/319,292, filed Oct. 6, 1994, now U.S. Pat. No. 5,595,324, which is a continuation-in-part of U.S. patent application Ser. No. 08/024,448, filed Mar. 1, 1993, now U.S. Pat. No. 5,379,917.

INCORPORATION BY REFERENCE

U.S. patent application Ser. No. 10/253,348, filed Sep. 24, 2002, U.S. patent application Ser. No. 09/544,011, filed Apr. 6, 2000, U.S. patent application Ser. No. 09/019,252, filed Feb. 5, 1998, U.S. patent application Ser. No. 08/730,364, filed Oct. 14, 1996, U.S. patent application Ser. No. 08/319, 292, filed Oct. 6, 1994, and U.S. patent application Ser. No. 08/024,448, filed Mar. 1, 1993, are hereby incorporated by reference herein in their entireties and made a part of this specification.

FIELD OF THE INVENTION

The present invention relates to soap dispensers, air fresheners, and supply units therefor and, in particular, to such dispensers used in washrooms and similar settings.

BACKGROUND OF THE INVENTION

Air freshener dispensers are often used in public washrooms to control odor in the enclosed area. Although air fresheners are sometimes referred to as scented or unscented, in reality all air fresheners give off a fragrance, and it is simply a matter of degree as to whether the air freshener is perceived as having its own scent or merely masking the undesirable odor in the washroom.

Air fresheners may be dispensed continuously, at regular intervals, or in response to a particular event, such as when the light in the washroom is turned on. The air freshener is typically dispensed from a source of fragrance through evaporation or atomization. The air freshener dispenser is usually located high on the washroom wall where suitable air flow exists to accelerate the dispensing of the air freshener. This location has the further advantage of preventing atomized air freshener from being sprayed directly on people using the washroom. Unfortunately, when the air freshener is dispensed in high places it tends to rise to the ceiling where it can be suctioned from the washroom via the ventilation system before it can control odor.

Due to its awkward location, maintenance personnel are sometimes unable to detect when the air freshener needs to be replaced. Furthermore, the placement of air freshener high on the wall requires maintenance personnel to stand on a ladder or platform in order to service it. While some air freshener dispensers have a beeping noise or blinking light to indicate that the supply of air freshener needs to be replaced, even with these replacement reminders, air freshener dispensers are frequently not maintained on a regular basis due to the inconvenience of maintaining the air freshener.

SUMMARY OF THE INVENTION

Applicant's invention overcomes the drawbacks of the prior art by providing a dual dispenser for soap and air freshener. For hygienic and cost reasons, soap dispensers, rather than individual bars of soap, are commonly used in public washrooms. They are usually located near the wash basin within easy reach of a person standing in front of a wash basin. Typically, the soap dispenser will include an actuating plate, which is pushed or pulled to dispense a measured quantity of soap into the person's hand.

Numerous advantages are realized through use of the dual dispenser and practicing the methods of the present invention. Significantly, Applicant's invention includes a method of facilitating the replacement of a supply of air freshener every time a supply of soap is replaced, including the steps of providing a supply of air freshener, providing a supply of soap and joining the supply of soap and the supply of air freshener. This substantially increases the likelihood that odor in the washroom or other environment will be controlled. For example, health regulations require that numerous establishments, such a restaurants and hospitals maintain a supply of soap in their washrooms to reduce the spread of disease. Accordingly, by joining the supply of soap to the supply of air freshener, the air freshener will be changed each time the supply of soap is changed.

Another aspect of the invention is a method of reducing the time necessary to maintain a supply of soap and a supply of air freshener, including the steps of providing a supply of soap, providing a supply of air freshener and inserting the supply of soap and the supply of air freshener into a single dispenser.

Yet another aspect of the invention is a method of packaging a supply unit including providing a supply of soap and a supply of air freshener and connecting the supply of soap and the supply of air freshener in a manner such that when the supply of soap is removed from a dispenser, the supply of air freshener is removed from the dispenser as well. Advantageously, the method may also comprise connecting a power source to one of the supply of soap or the supply of air freshener in such a manner that when one of the supply of soap or the supply of air freshener is removed from a dispenser, the source of power is removed from the dispenser.

Importantly, yet another aspect of the present invention is a method of efficiently utilizing air freshener, including providing a receptacle, inserting a supply of soap into the receptacle and connecting a supply of air freshener to the receptacle in an amount calculated to provide sufficient air freshener to last as long as the supply of soap. Finally, yet another aspect of the invention is a method of effectively utilizing air freshener including a supply of soap, providing a supply of air freshener, connecting the supply of soap and the supply of air freshener to an actuator, and dispensing a portion of the supply of soap and a portion of the supply of air freshener when the actuator is actuated.

Another aspect of the present invention is a supply unit for the dual dispenser including a receptacle, a supply of soap within the receptacle, and a supply of air freshener connected to or secured within the receptacle. Advantageously, the supply unit further includes a source of power mounted to the receptacle.

Finally, yet another aspect of the invention is a dual dispenser including means for dispensing the soap, means for actuating the dispensement of soap, means for accelerating the dispensement of air freshener and means for actuating the means for accelerating the dispensement of air freshener.

As will be understood by those of skill in the art from the nature of the invention and the specification, "source of fragrance" used in this application means a supply of air freshener. That is, the source of fragrance which is included in the supply unit and dispensed by the dispenser of the present invention will be understood as meaning a source of air freshener. As is known by those of skill in the art, the chemical composition of an air freshener will vary depending upon various factors, including the nature of the fragrance utilized by the air freshener. Specifically, while air fresheners typically comprise 10–25% fragrance, they may utilize as little as 3% fragrance, if the fragrance is particularly strong. Furthermore, they may utilize a higher percentage of fragrance if the fragrance is particularly mild. Since fragrance is typically relatively expensive, the air freshener will usually utilize a "carrier," such as an odorless mineral spirit to dilute the fragrance and to aid in evaporation. The nature of fragrance used in the air freshener will depend upon numerous factors including the nature of the odors expected to be controlled, and numerous industry reference materials are available which describe the nature of fragrance desirable to control certain odors.

These and other aspects of the present invention will now be described with reference to an improved embodiment, which is intended to illustrate and not to limit the invention.

DESCRIPTION OF THE PREFERRED EMBODIMENTS

Figure 1:
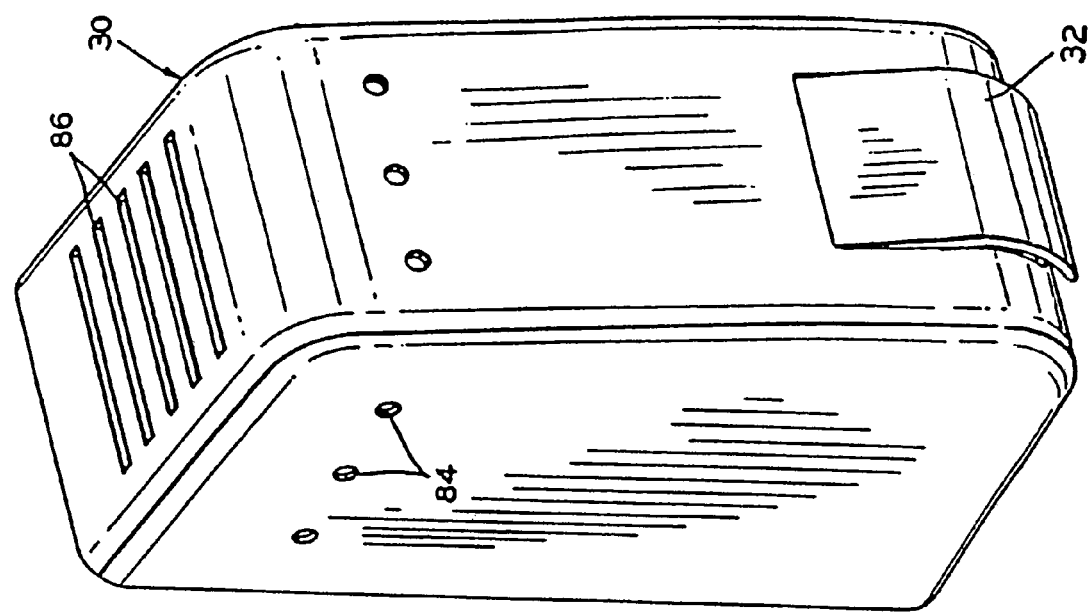
FIG. 1 is an exploded perspective view of one embodiment of a dual soap/air freshener dispenser of the present invention.
Figure 1:
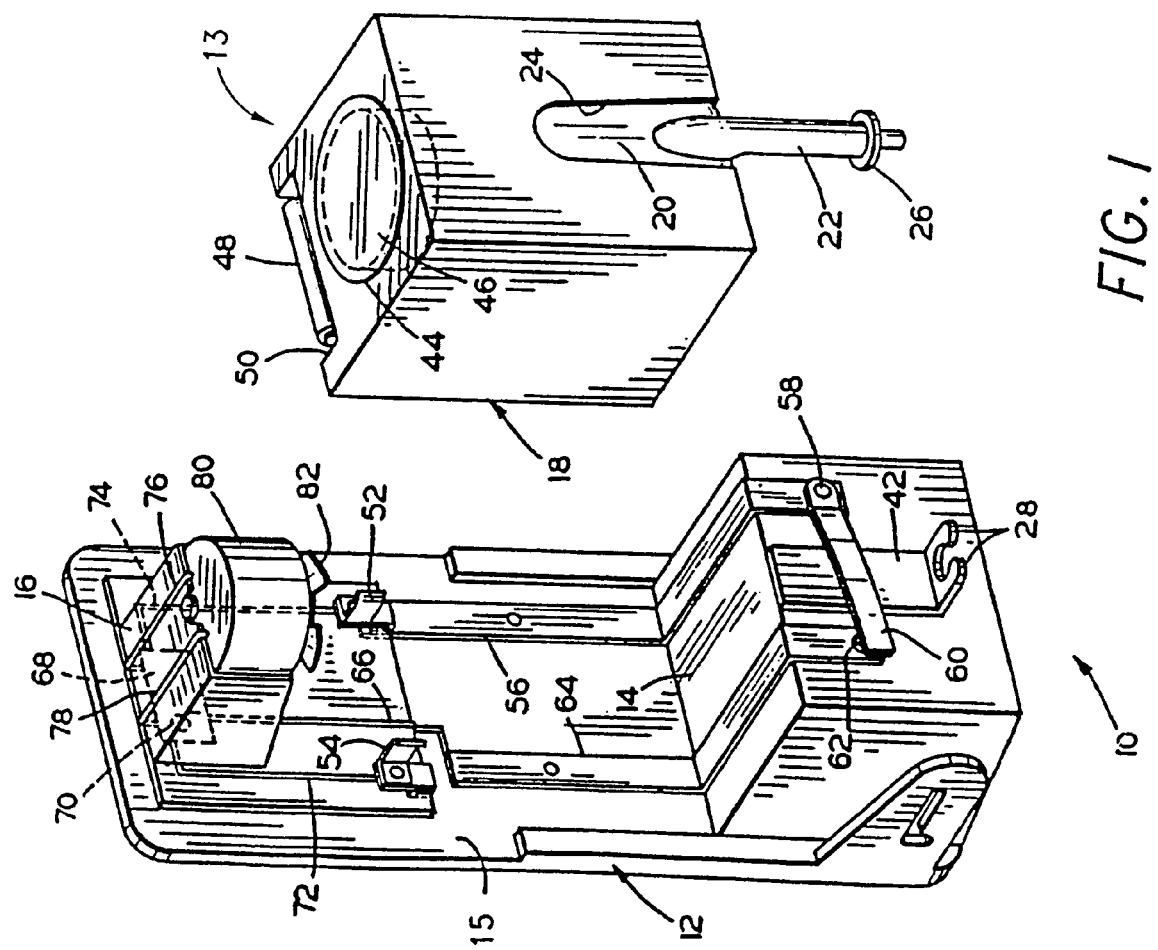

With reference to FIG. 1, a dual soap/air freshener dispenser according to the present invention is indicated in an exploded view at 10. The dual dispenser 10 comprises a mounting plate 12 for attaching to a wall, a supply unit 13 containing containers for soap and air freshener, and a cover 30. The mounting plate 12 includes a rear vertical wall plate 15 having both a lower shelf or support 14 and an upper support 16 extending forwardly therefrom. The supply unit 13 includes a generally rectilinear protective box 18 enclosing a flexible bag 20 of liquid soap. A flexible dispensing tube 22 is opened to the interior of the bag 20 and extends downward from a lower portion of the bag.. The dispensing tube 22 extends through an opening 24 in the enclosing box 18 and has a flanked spout 26. For shipping purposes, the box 18 is originally fully enclosed, but a section (not shown) defined by a perforation is removed to define the opening 24 in the box 18. The dispensing tube 22 can be pulled out from a folded condition within the box 18 prior to placing the box in the mounting plate 12. When installed, the box 18 is supported by the shelf 14 below the upper support 16. The dispensing tube 22 depends downwardly so that the flanked spout 26 is inserted between clips 28 at a lower portion of the mounting plate 12.

Figure 2:
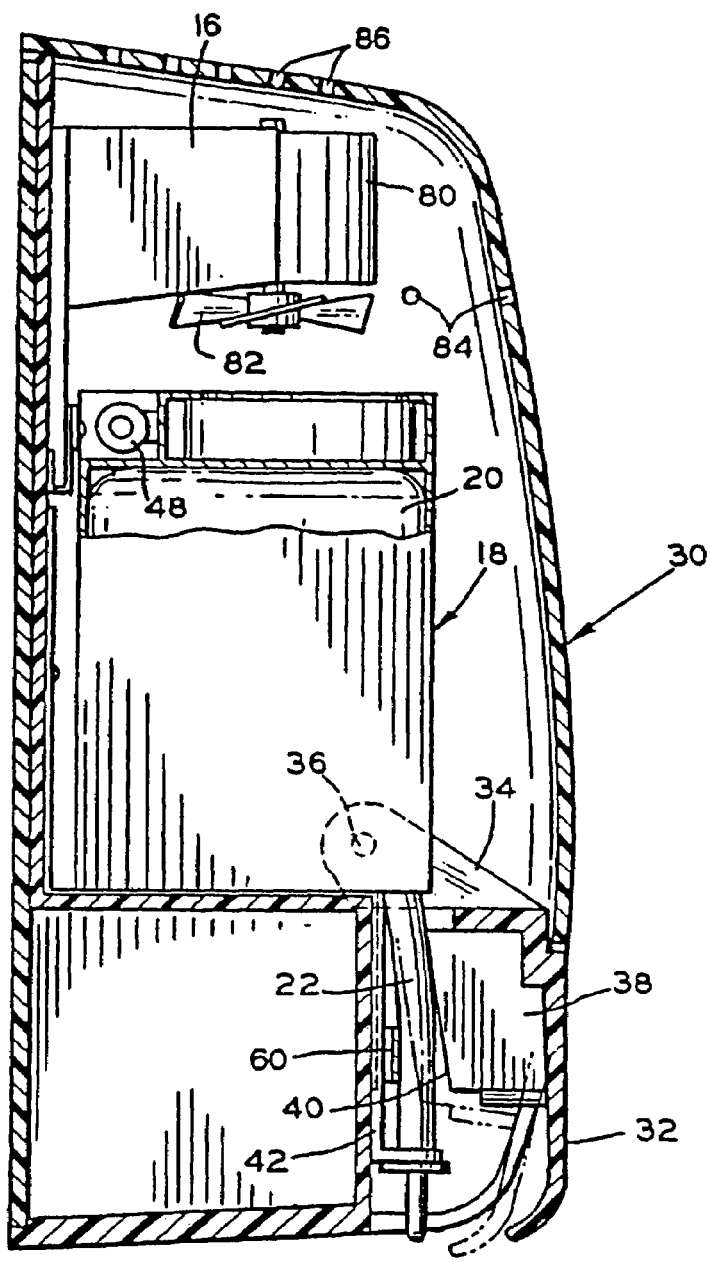
FIG. 2 is a cross-sectional, elevational view of the assembled dual soap/air freshener dispenser of FIG. 1.

The cover 30 for the dual dispenser 10 includes an actuating plate 32 pivotably attached at a lower front portion. More particularly and with reference to FIG. 2, the actuating plate 32 includes a pair of brackets or ears 34 having throughholes for mounting on a rod or pair of rod stubs 36 formed on the inner surface of the cover 30 and generally aligned transversely across the cover. A squeeze bar 38 is attached to the actuating plate 32 between the ears 34. The squeeze bar 38 includes a rear slanted surface 40 which impinges against the downwardly depending dispensing tube 22, forcing it against a front surface 42 of the mounting plate 12 when the actuating plate 22 is depressed inward from the front of the cover 30. This motion can be seen in phantom in FIG. 2.

The supply unit 13 includes a container 44 mounted in an upper portion. The container 44 holds a supply of air freshener, such as gel 46. A battery 48 is mounted within a rear recess 50 of the supply unit 13. The battery is firmly attached at a central location within the recess 50 to provide small gaps on either end of the battery. A pair of electrical contacts 52, 54 provided on the front of the wall plate 15 are positioned and sized to extend within the gaps and make contact with the electrical terminals of the battery 48. The electrical contact between the battery 48 and the terminals 52, 54 is accomplished when the supply unit 13 is mounted on the mounting plate 12. A removable lid or top (not shown) is provided on the container 44 and is removed prior to installing the supply unit 13 on the mounting plate 12 to expose the fragrant gel 46.

The contact 52 is in electrical connection with a conducting strip 56 extending downward along the wall plate 15. The strip 56 continues forwardly over the lower support 14 and to a front surface 42 to join with a fastener 58. The fastener 58 connects the conducting strip 56 with a switchblade or strip 60 arranged transversely across the front surface 42. The switchblade 60 is positioned to the rear of the flexible dispensing tube 22 when the supply unit 13 is installed. When the actuating plate 32 is depressed from the front, the squeeze bar 38 causes the dispensing tube 22 to press against the switchblade 60 and force it into electrical contact with a terminal 62. The terminal 62 is in electrical connection with a conducting strip 64 which extends upward to a PC board 68 having a solid-state timer 70. A conductor 72 also electrically connects the contact 54 with the PC board 68. To complete the circuit, a conductor 74 electrically connects the PC board 68 with the contact 52.

Conductors 76 and 78 extend forward from the PC board 68 to a small, commercially available electric motor 80 is positioned in the upper support 16 and above the supply unit 13 when installed. The motor 80 drives a small fan 82 directly above the container 44. When the fan 82 rotates, it circulates air over the container 44 and gel 46 to disperse air freshener through side openings 84 and upper slits 86 in the cover 30.

Figure 3:
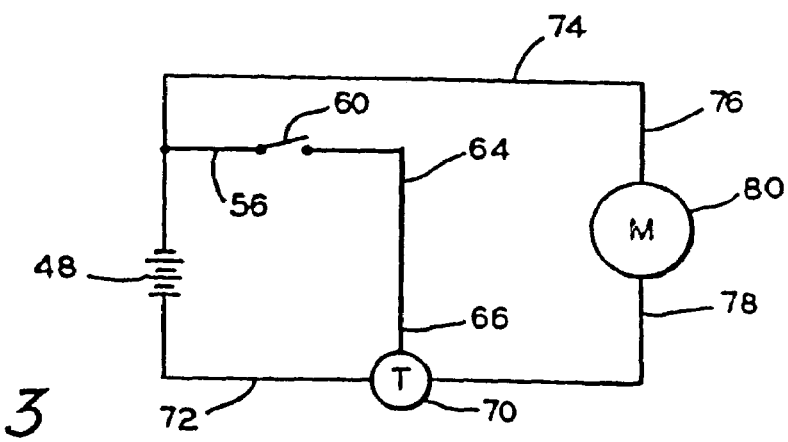
FIG. 3 is a circuit diagram used in operating the dual soap/air freshener dispenser.

Now with reference to the circuit diagram of FIG. 3, the switchblade 60 provides closure to a timer circuit. The timer 70 conducts for a predetermined period of time, such as, for example, 15–20 seconds. The timer completes a circuit for this predetermined period of time through the battery 48 and motor 80. The timer 70 can also be a chip which is programmed to periodically operate the motor 80 and fan 82 for a given period of time. Furthermore, the motor 80 and fan 82 could be run continuously for use in areas with high odor problems. The dual dispenser 10 may also include an LED indicator which is turned on when the motor 80 is running. In place of the motor 80 and fan 82, a heat-activated material could be used to melt a plastic bar which is impregnated with air freshener. This would be accomplished by powering the unit with a battery or through a direct electrical wall connection. The dispenser 10 can also be used with a light-sensitive eye to turn the motor 80 and fan 82 on when the lights in the room are on.

In place of positioning the air freshener container 44 in the top of the supply unit 13, a separate plastic shroud could be employed which fits over the top of a standard box 18, with the shroud housing both the battery 48 and source of fragrance. A dispenser with the fragrance source could also be used with a reservoir type of soap dispenser, rather than a separate soap box.

Description of Another Dual Soap/Air freshener Dispenser Embodiment

Figure 4:
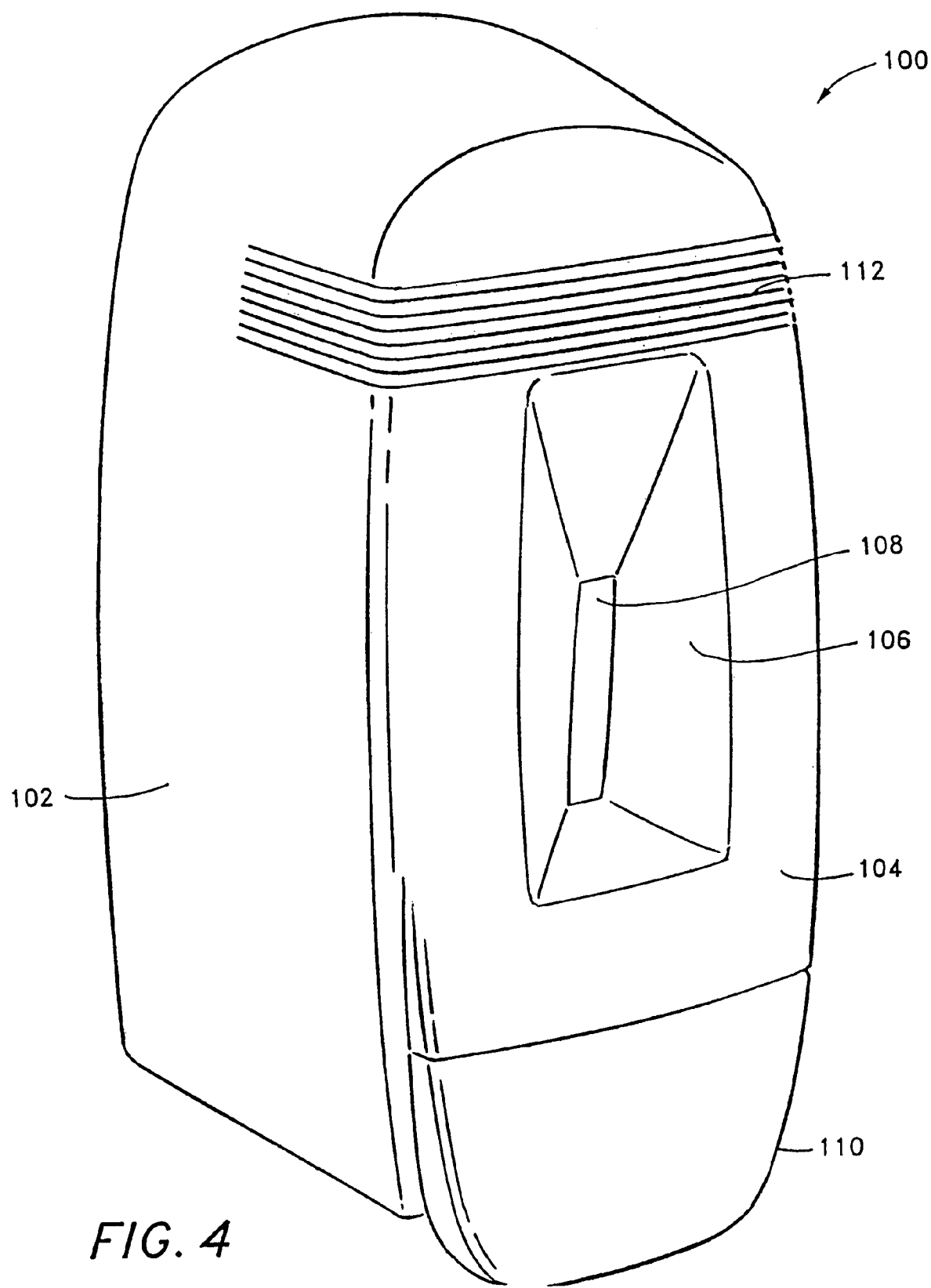
FIG. 4 is a perspective view of a second embodiment of the dual soap/air freshener dispenser of the present invention.

With reference to FIG. 4, a second embodiment of a dual soap/air freshener dispenser includes a front cover 100. The cover 100 comprises a generally oval-shaped outer side wall 102 and a front wall 104. A recess 106 in the front wall 104 supports an elongated vertical window 108. A movable actuator plate 110 is pivotably mounted to the cover 100, as will be explained more fully below with respect to FIG. 8. The cover 100 also includes a series of horizontally aligned ducts 112 providing communication between the interior and the exterior of the cover.

Figure 5:
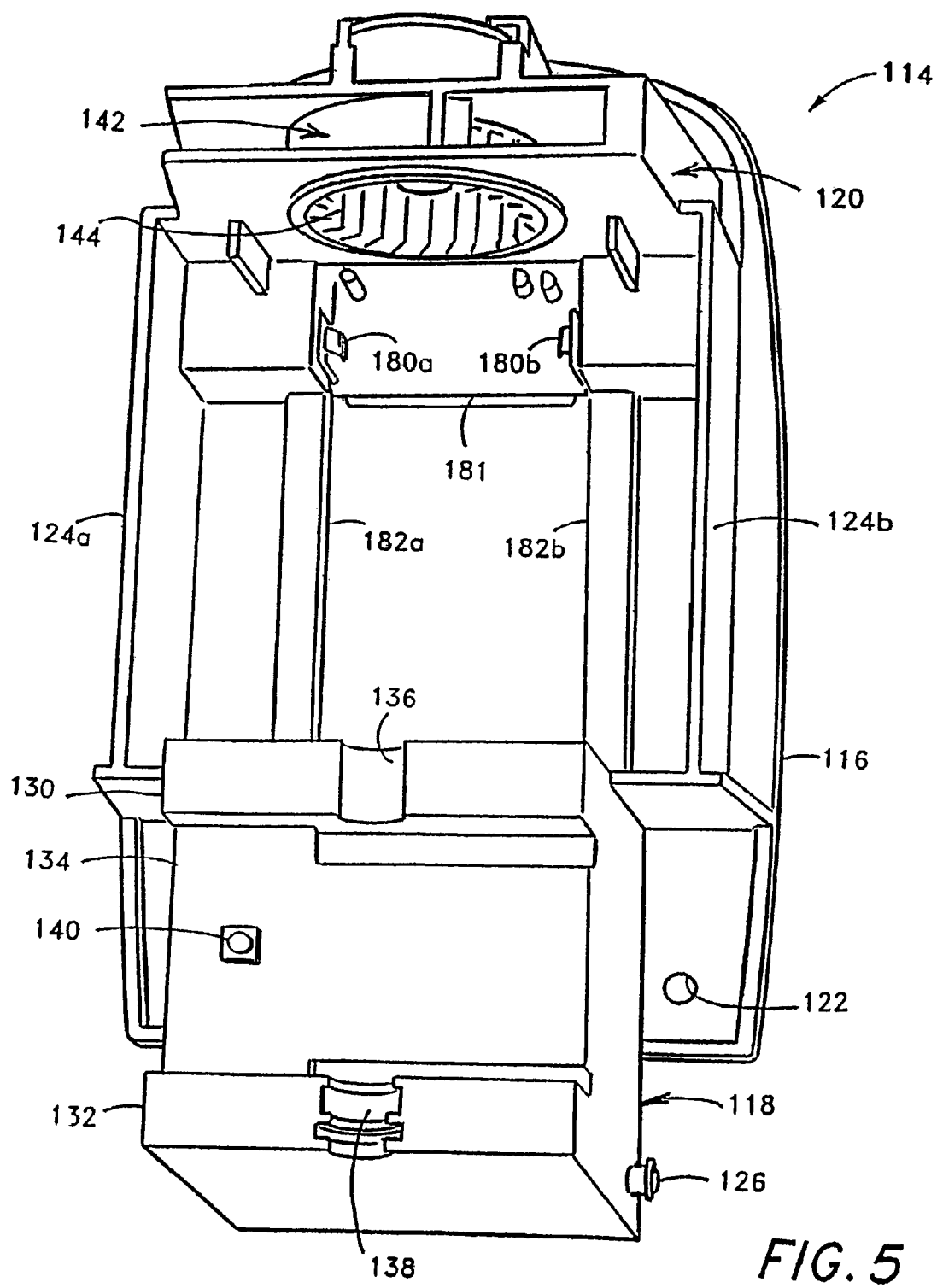
FIG. 5 is a perspective view of a base portion of the dual soap/air freshener dispenser of FIG. 4.
Figure 6:
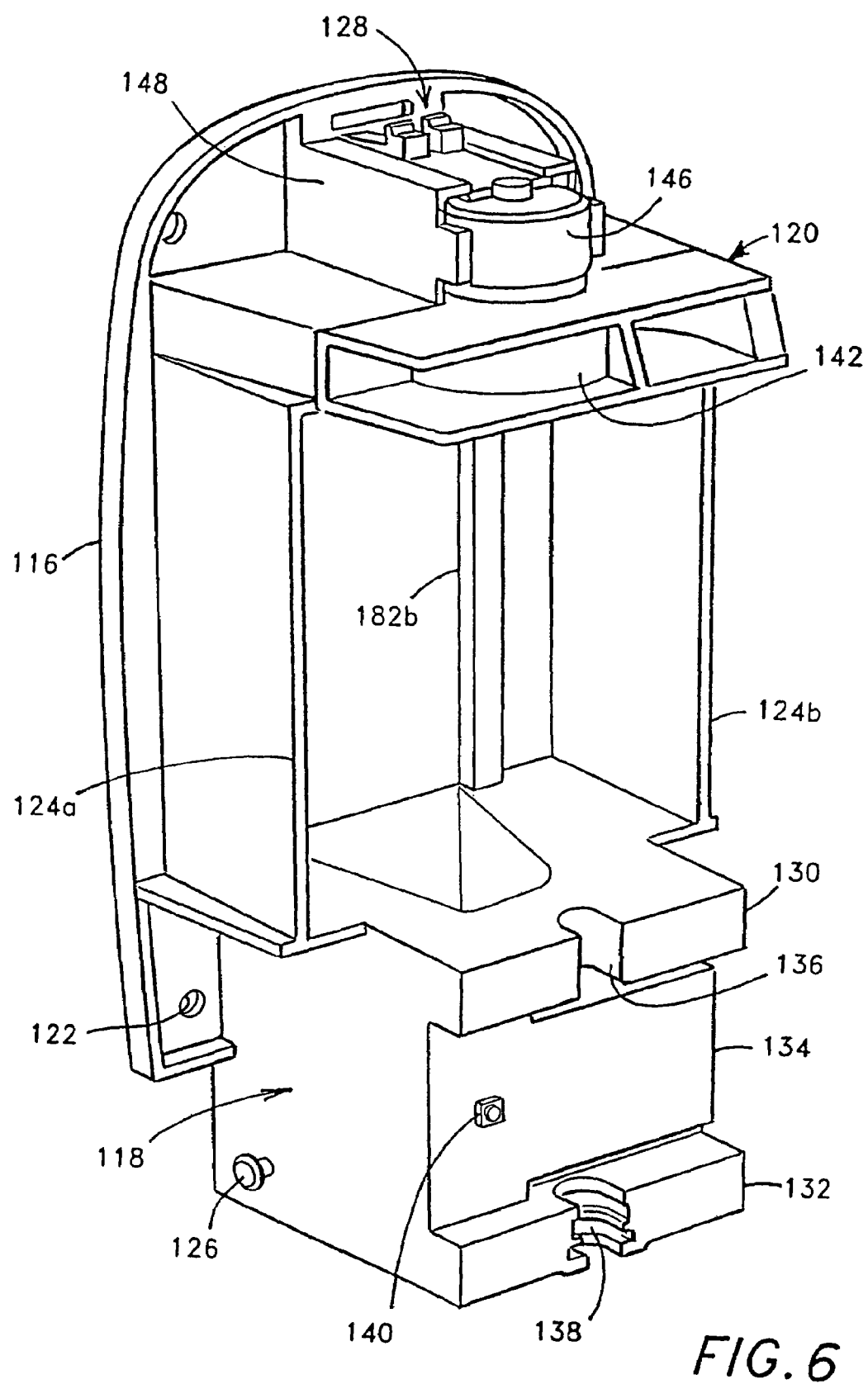
FIG. 6 is a lower, front perspective view of the base portion of FIG. 5.

Now with reference to FIGS. 5 and 6, the cover 100 is adapted to be mounted over a base 114. The base 114 generally comprises a rear vertical wall plate 116 having a hollow lower support 118 and an upper support 120 extending forwardly therefrom. The wall plate 116 includes a series of mounting holes 122 for attaching the base 114 to a wall in a washroom or other such location. The base 114 includes a pair of opposed side walls 124*a*, 124*b* which, together with the lower support 118 and upper support 120, define a supply unit housing. The supply unit 150 will be described below with reference to FIG. 7.

As mentioned, the cover 100 is adapted to be mounted to the base 114. In this regard, a pair of cover pivot stubs 126 are provided on either side of the lower support 118. These pivot stubs 126 are adapted to extend into cylindrical cavities (not shown) on the lower interior sides of the outer wall 102 of the cover 100. A cover latch 128 (FIG. 6) mates with a complementary latch (not shown) provided on the upper interior of the outer wall 102 of the cover 100. Thus, the cover 100 can be released and pivoted downward, away from the base 114 about the pivot stubs 126.

The lower support 118 comprises a generally box-shaped member extending forward from the wall plate 116 and defining at its forward distal end an upper ledge 130, an abutment wall 134, and a lower ledge 132. The abutment wall 134 is recessed rearwardly from both the upper and lower ledges 130, 132. A generally cylindrical relief 136 is formed in the upper ledge 130. Likewise, a generally cylindrical brace relief 138 is formed in the lower ledge 132. The brace relief 138 includes a circular groove therein, which purpose will be described below. A switch 140 is positioned on the abutment wall 134 and includes an actuator button or other such switching device facing forward thereon.

The upper support 120 extends forward from the wall plate 116 and over the supply unit housing defined between the side walls 124*a,b*. A centrifugal fan 142 having fan blades 144 is rotatably positioned within an aperture in the upper support 120. A motor 146 mounted within brackets 148 in the upper support 120 is coupled to rotate the centrifugal fan 142.

Figure 7:
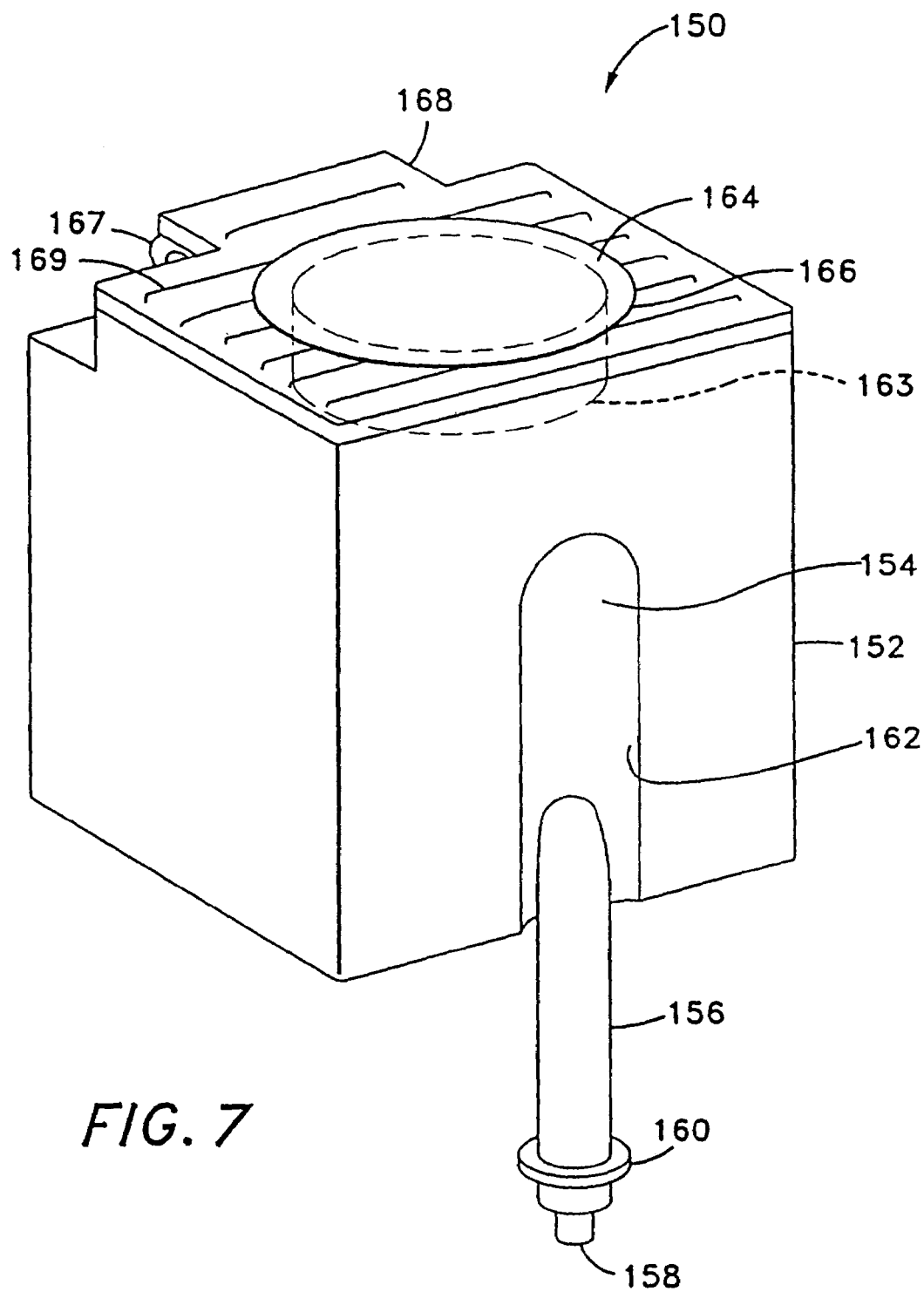
FIG. 7 is a perspective view of a removable supply unit containing soap and air freshener for use in the dispenser of FIG. 4.

Now with reference to FIG. 7, a preferred supply unit 150 is shown. The supply unit 150 includes containers for both soap and an aromatic air freshener. The supply unit 150 is generally defined by an outer protective box 152 enclosing a flexible container or bag 154 therein. The box 152 may be cardboard or other suitable material. A flexible dispensing tube 156 is attached to a lower front corner of the container 154. The tube 156 terminates in an outlet 158 and includes a lower collar or flange 160. A valve (not shown) is positioned within the outlet to prevent the release of fluid from the tube 156 unless sufficient pressure is exerted. For storage and shipping, the dispensing tube 156 is folded upward against a front wall of the container 154 and within the box 152. A section (not shown) of the box 152 is detached at a perforated score line to form an elongated aperture 162. Once the aperture 162 is formed, the dispensing tube 156 can be retracted from inside the box 152 and assume a downwardly depending orientation, as shown in FIG. 7.

The supply unit 150 also houses a air freshener 10 container 163 above the flexible container 154. The air freshener container 163 includes a lid 164 made of foil or other such disposable material. The lid 164 is adapted to easily removed from the container 163 prior to use. The lid 164 extends over a lip portion 166 on the container 163. The is battery 167 is mounted centrally on a rear ledge 167 of the box 152. An upper plate 164 covers the container 163 and battery 167. The lip portion 166 of the container 163 may rest directly on top of the plate 168 or may lie flush with the plate in a stepped recess (not shown). Alternatively, the container 163 may be securely attached to the upper plate 168. The container 163 itself may be approximately 2.7 inches in diameter. The rearwardly extending portion of the upper plate 168 covers and protects the battery 167. The plate 168 includes a series of ribs 169 which provide strength and prevent warping during the manufacturing process.

Figure 8:
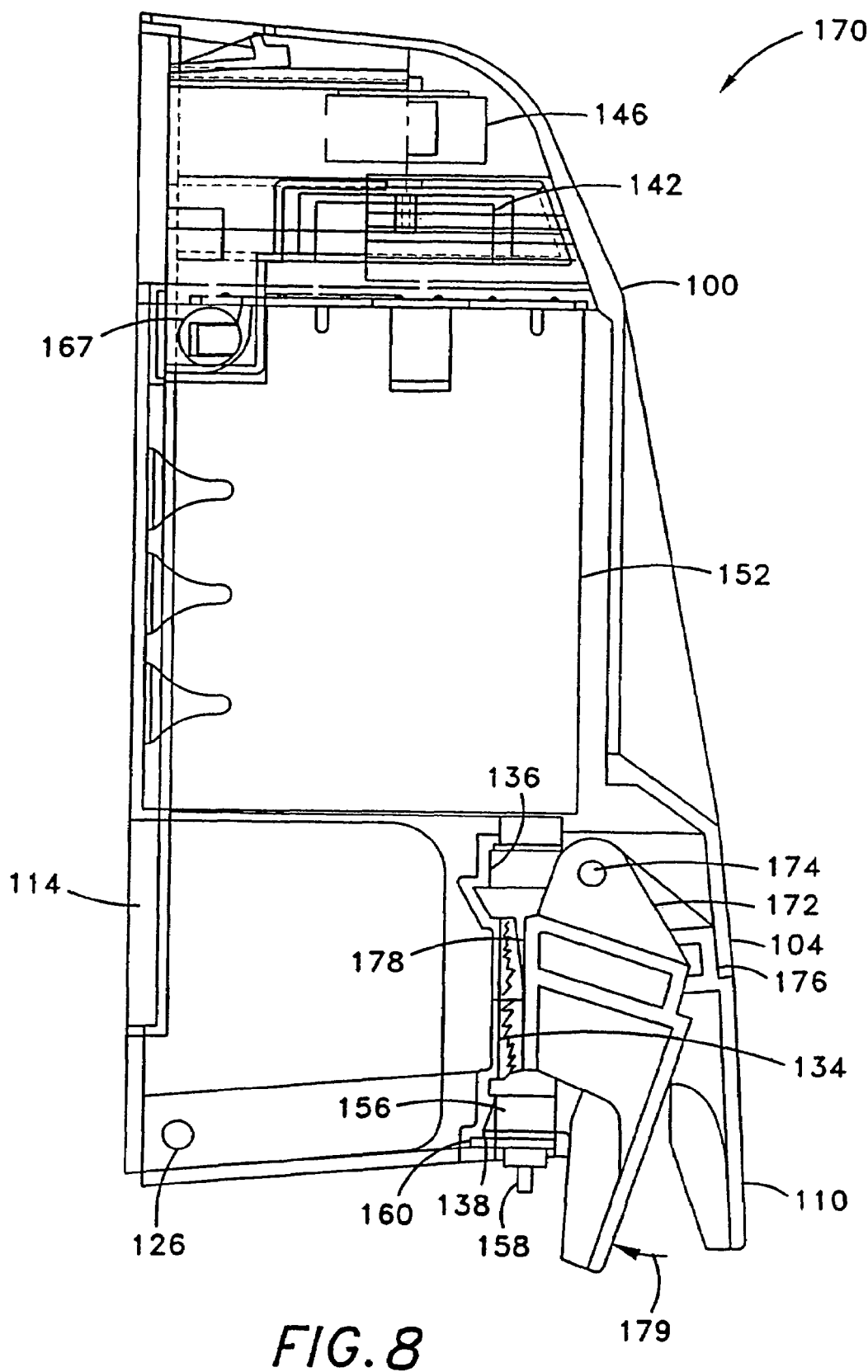
FIG. 8 is a cross-sectional view of the dual soap/air freshener dispenser of FIG. 4 showing the motion of an actuating plate in phantom.

With reference to FIG. 8, the assembled dual soap/air freshener dispenser 170 is illustrated. The cover 100 is shown mounted over the base 114. The box 152 containing the containers 154 and 163 is positioned within the housing defined by the base 114. In this position, the dispensing tube 156 depends downwardly and is located within the relief 136 and brace relief 138 previously described. In this manner, the flange 160 fits within the groove formed in the brace relief 138 to secure the end of the dispensing tube 156 against vertical movement. The outlet 158 extends downwardly from the bottom of the dual dispenser 170.

The action of the actuator plate 110 is illustrated in FIG. 8. More particularly, the actuator plate includes a pair of upwardly extending side brackets 172 having apertures therein. The apertures fit over a pair of pivot rods 174 formed in the inner side of the side walls 102 of the cover 100. The actuator plate 110 includes a step structure 176 which contacts a portion of the front wall 104 of the cover 100. The actuator plate further includes a rear squeeze plate 178 facing the abutment wall 134 of the lower support 118. The dispensing tube 156 is thus positioned between the abutment wall 134 and the squeeze plate 178. When the actuator plate 110 pivots rearwardly, as shown by arrow 179, by depressing from the front of the dual dispenser 170, the squeeze plate 178 comes into contact with the dispensing tube 156. The squeeze plate 178 forms an acute angle with the forward lower and of the actuator plate, causing the squeeze plate to first come into contact with the dispensing tube at an upper portion. As the actuator plate 110 is pushed inward, the squeeze plate 178 gradually comes into greater surface contact with the dispensing tube 156, causing a specified volume of liquid soap therein to be expelled through the outlet 158. The valve in the outlet 158 prevents dripping of the relatively viscous liquid soap therein until overcome by the pressure of this dispensing action. Upon release of the actuator plate, gravity causes the liquid soap within the container 154 to fill the dispensing tube 156 once again. The actuator plate 110 will also be gradually pushed outward to its initial position.

Referring to FIG. 5, 6 and 8, full depression of the actuator plate 110 also causes the squeeze plate 178 to come into contact with the air freshener dispensing switch 140. Actuation of the air freshener dispensing switch 140 turns the motor 146 on for a predetermined period of time. This is accomplished through a circuit similar to that shown in FIG. 3. More particularly, the supply unit housing includes a pair of battery terminals 180a, 180b extending forward from a PC board 181 and positioned to contact the terminals of the battery 167 mounted in the supply unit 150. Thus, when the supply unit 150 is inserted into the housing defined between the side walls 124a,b, the battery 167 forms an electrical connection between the terminals 180a,b. A pair of conduits 182a, 182b extends downward from the upper support 120 to the lower support 118. These conduits 182a,b contain electrical conductors between the air freshener dispensing switch 140 and the PC board 181 within the upper support 120.

As discussed above, an important aspect of the invention is the coordination of the volume of the supply of soap and the supply of air freshener to ensure that the supply of air freshener is sufficient to continue freshening the air the entire period soap is available in the supply unit. Furthermore, in addition to ensuring that there is a sufficient supply of air freshener to control odor until the supply of soap is exhausted, the present invention permits the supply of air freshener to be limited to an amount just sufficient to continue freshening the air until the supply of soap is exhausted. In a first embodiment, for example, the total volume of the supply of soap is 700 milliliters and the total volume of the supply of air freshener is 26.2. These amounts were determined by dividing a standard volume for a supply of soap, 700 milliliters, by the desired volume of soap dispensed each time the actuator bar is depressed, 1 milliliter, to determine the number of times the actuator bar will be depressed before the supply of soap is exhausted. The desired volume of air freshener dispensed each time the actuator bar is depressed, 0.026 milliliters, is then multiplied by the number of times the actuator bar will be depressed to exhaust the supply of soap, then a reasonable safety margin, to account for evaporation when the fan is not activated, is added to determine the desired volume of air freshener, in this case approximately 26.2 milliliters.

In an alternative embodiment for a larger volume supply unit, the total volume of the supply of soap is 900 milliliters and the total volume of the supply of air freshener is 33.6. As before, the number of times the actuator bar is depressed before the supply of soap is exhausted is found by dividing the volume of soap by the volume of soap dispensed each time the actuator bar is depressed. The desired volume of air freshener dispensed each time the actuator bar is depressed is then multiplied by the number of times the actuator bar will be depressed to exhaust the supply of soap. A reasonable safety margin is added to determine the desired volume of air freshener, in this case approximately 33.6 milliliters. As will be appreciated by those of skill in the art, these numbers will vary significantly, depending upon various factors such as the carrier utilized by the air freshener, the expected environmental conditions, etc. Indeed, it may be desirable to empirically determine the particular volumes of soap and fragrance required.

In either size dispenser discussed above, the desired volume of air freshener dispensed each time the actuator bar is depressed, is used to determine the length of time the fan must run to dispense the desired volume of air freshener. In either embodiment, it has been determined, given the volume of air flow from the fan, that the fan should ideally run 45 seconds each time the actuator bar is depressed. Of course, other time periods for different fans may be utilized. A preferred fan for use in the present invention includes a blower wheel with a 2" diameter and a height of ⅝". Additionally, the motor rotates the blower wheel at 2200–2600 rpm. One example of such a fan is model NISSEI DENKI M663-GF distributed by Douglas International of Geneva, Ill.

Another beneficial aspect of the present invention is the optimum positioning of the source of fragrance in a washroom or other room. Prior fragrance dispensers were often located high in the room near ceiling fans which diluted their effect. Indeed, aerosol fragrance dispensers are placed high up as a safety precaution to prevent direct facial exposure to the aerosol mist. The present dispenser, on the other hand, is situated low on the wall within easy reach of people. Because the fragrance is dispensed so close to the user, less fragrance is needed to accomplish the same effect. Importantly, the fragrance is dispensed "on demand" rather than continuously or at regular intervals. This also increases the efficiency of the system by minimizing the quantity of fragrance needed.

Another cost benefit associated with the dual soap/fragrance dispenser described herein is the complete elimination of a separate fragrance dispenser. Although not often required by law, fragrance dispensers in public washrooms are desirable and nearly universally provided in some form or another. The dual soap/fragrance dispenser costs somewhere between the cost of a typical soap dispenser alone and the cost of a soap dispenser and a fragrance dispenser combined. In conjunction with the automatic fragrance replacement feature of the present dispenser, this cost savings is highly attractive.

Although described and illustrated in terms of a air freshener container 163, a source of air freshener may be in other forms. For example, the air freshener may be in the form of a solid stick or bar which emits a fragrance upon being heated. An electrode or heating element may replace the motor 180 and fan 182 in this configuration. In a different configuration, the motor and fan may be eliminated altogether, and depression of the switch 140 may cause a ventilation door in the cover 100 to open, with the air freshener being dispersed naturally without forced air. In this regard, the cover 100 of the disclosed embodiment forms an extremely effective shroud over the air freshener container 163 to prevent air flow which would otherwise result in the premature evaporation of the air freshener therein. As mentioned previously, the amount of air freshener within the container 163 is carefully measured to last as long as the soap within the container 154 lasts. The longevity of the air freshener within the container 163 is also dependent on the amount of time for which the fan 182 is turned on each time someone depresses the actuating plate 110. In a further configuration, an air freshener source in the form of a pump dispenser may be substituted for the air freshener container 163. In this embodiment, depressing the actuation plate 110 causes either a manual or electrically actuated lever to depress the pump of the air freshener dispenser.

The preferred form of the air freshener in the container 163 is generally described as an odorless carrier with a particular concentration of fragrance therein. Typical air fresheners of this composition utilize a concentration of fragrance of between 5–50%, and sometimes as low as 3%. Most brands of air freshener of this type are between 10–25% concentration of fragrance, however. In the preferred embodiment, the air freshener comprises 30% fragrance and 70% odorless mineral spirit carrier, such as manufactured under the trade name ISOPAR K or G, manufactured by Exxon Corp. Although many types of fragrance are possible, the preferred fragrance is a mild high lift fragrance manufactured by International Fragrances, Inc. of Houston, Tex., and may be fragrance No. FG 9798. This higher percentage of fragrance than normal is desirable due to the relatively mild nature of the fragrance.

To prevent the relatively volatile carrier in air freshener from spilling from the container 163 when the foil lid 164 is removed, a polyester matrix is provided therein, and the fragrance and carrier saturated within the matrix.

Although it is not necessary to use any particular form of soap with the broadest aspects of the present invention, it is preferable that the soap be pourable. Desirably, the supply of soap utilized is a liquid hand soap. In particular, it is desirable to utilize a nonionic or anionic phenol. Although such soaps are sometimes scented, they have a much lower concentration of fragrance than would an air s freshener. Specifically, a hand soap would generally have a maximum of 0.5% fragrance for various reasons, including the risk of allergic reaction by users. More typically, the soap would have no more than a concentration of 0.25% fragrance and, the preferred supply of soap has only 0.15% fragrance. Advantageously, by packaging soap and air freshener together in a single supply unit, one can ensure the compatibility of any fragrance contained in the soap.

Although this invention has been described in terms of certain preferred embodiments, other embodiments that are is apparent to those of ordinary skill in the art are also within the scope of this invention. Accordingly, the scope of the invention is intended to be defined by the claims that follow.

We claim:

1. A supply unit for a soap dispenser, comprising:
    a box defining an interior space sized and shaped to receive a supply of liquid soap, said box having an open upper end, a forward side of said box including a section defined by a perforated score line configured to define an aperture when said section is detached from said box, said aperture configured to permit said supply of liquid soap to be dispensed from said box, an external surface of a rearward side of said box defining a recess that receives and securely supports a battery outside of said interior space in a fixed position relative to said box;
    a bag containing a supply of soap placed within said interior space of said box; and
    a plate sized and shaped to cover said open upper end;
    wherein at least terminal ends of the battery received within said recess are externally accesible when said plate is positioned to cover said open upper end of said box.

2. The supply unit of claim 1, wherein said plate extends over said recess.

3. The supply unit of claim 2, wherein said recess extends an entire width of said box.

4. The supply unit of claim 1, wherein said plate is a separate member from said box.

5. The supply unit of claim 1, wherein said plate includes a plurality of strengthening ribs.

\* \* \* \* \*